US012678223B2

(12) United States Patent (10) Patent No.: US 12,678,223 B2
Rodriguez Soto et al. (45) Date of Patent: Jul. 14, 2026

(54) SYSTEMS AND METHODS FOR CYLINDRICAL CAGE MAPPING AND ABLATION CATHETERS HAVING FLEXIBLE CIRCUITS

(71) Applicant: Biosense Webster (Israel) Ltd., Yokneam (IL)

(72) Inventors: Juan Rodriguez Soto, Irvine, CA (US); Mohammad Abbas, Orange, CA (US); Babak Ebrahimi, Lake Forest, CA (US); Pieter Emmelius Van Niekerk, Rancho Santa Margarita, CA (US); Shubhayu Basu, Anaheim, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 258 days.

(21) Appl. No.: 18/509,788

(22) Filed: Nov. 15, 2023

(65) Prior Publication Data

US 2024/0216052 A1     Jul. 4, 2024

Related U.S. Application Data

(60) Provisional application No. 63/477,754, filed on Dec. 29, 2022.

(51) Int. Cl.
*A61B 18/14* (2006.01)
*A61B 5/00* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01);
(Continued)

(58) Field of Classification Search
None
See application file for complete search history.

(56) References Cited

U.S. PATENT DOCUMENTS 4,699,147 A    10/1987  Chilson et al.
4,940,064 A     7/1990  Desai
(Continued)

FOREIGN PATENT DOCUMENTS

CN         111248993 A     6/2020
CN         111248996 A     6/2020
(Continued)

OTHER PUBLICATIONS

Extended European Search Report and Opinion dated May 17, 2024, from corresponding European Application No. 23219781.4.

*Primary Examiner* — Joseph A Stoklosa
*Assistant Examiner* — Annie L Shoulders

(57) ABSTRACT

The disclosed technology includes a medical probe includes a substantially cylindrical structure having a proximal circular base, a distal circular base substantially parallel to the proximal circular base, a plurality of spines extending along a longitudinal axis between the proximal circular base and the distal circular base, and one or more strips of flexible circuit substrate coupled to one or more of the plurality of spines defining an internal volume about the longitudinal axis. The plurality of spines include a trifurcation point positioned along at least a portion of the spine and a spine branch extending from the trifurcation point further comprising a bifurcation point. The one or more strips of flexible circuit substrate further include one or more conductive traces disposed on a surface of the substrate.

19 Claims, 11 Drawing Sheets

(52) U.S. Cl.
CPC .............. *A61B 2018/00863* (2013.01); *A61B 2018/00964* (2013.01); *A61B 2018/1465* (2013.01); *A61B 2018/1467* (2013.01); *A61B 2018/1475* (2013.01); *A61B 2018/1497* (2013.01)

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A | 8/1995 | Ben-Haim | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,172,499 B1 | 1/2001 | Ashe | |
| 6,216,043 B1 | 4/2001 | Swanson et al. | |
| 6,216,044 B1 | 4/2001 | Kordis | |
| 6,239,724 B1 | 5/2001 | Doron et al. | |
| 6,332,089 B1 | 12/2001 | Acker et al. | |
| 6,428,537 B1 | 8/2002 | Swanson et al. | |
| 6,456,864 B1 | 9/2002 | Swanson et al. | |
| 6,484,118 B1 | 11/2002 | Govari | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,618,612 B1 | 9/2003 | Acker et al. | |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| 7,536,218 B2 | 5/2009 | Govari et al. | |
| RE41,334 E | 5/2010 | Beatty et al. | |
| 7,756,576 B2 | 7/2010 | Levin | |
| 7,846,157 B2 | 12/2010 | Kozel | |
| 7,848,787 B2 | 12/2010 | Osadchy | |
| 7,869,865 B2 | 1/2011 | Govari et al. | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |

(56) References Cited

U.S. PATENT DOCUMENTS

| | | | |
|---|---|---|---|
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,330,742 B2 | 6/2019 | Govari |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 11,304,642 B2 | 4/2022 | Govari et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0192958 A1* | 7/2018 | Mou .................... A61B 5/6858 |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |

(56)  References Cited

U.S. PATENT DOCUMENTS

| | | | |
|---|---|---|---|
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155224 A1 | 5/2020 | Bar-Tal |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0015551 A1 | 1/2021 | Fuentes-Ortega et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |

| | | | |
|---|---|---|---|
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0121231 A1* | 4/2021 | Basu .................. A61B 18/1492 |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2023/0012307 A1* | 1/2023 | Harlev ............... A61B 18/1492 |
| 2023/0380897 A1* | 11/2023 | Liu ........................ A61B 5/287 |

FOREIGN PATENT DOCUMENTS

| | | | |
|---|---|---|---|
| CN | 112754650 A | 5/2021 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |

(56)                  References Cited

FOREIGN PATENT DOCUMENTS

| | | | |
|----|------------|----|---------|
| WO | 2019143960 | A1 | 7/2019  |
| WO | 2020026217 | A1 | 2/2020  |
| WO | 2020206328 | A1 | 10/2020 |
| WO | 2021126980 | A1 | 6/2021  |

* cited by examiner

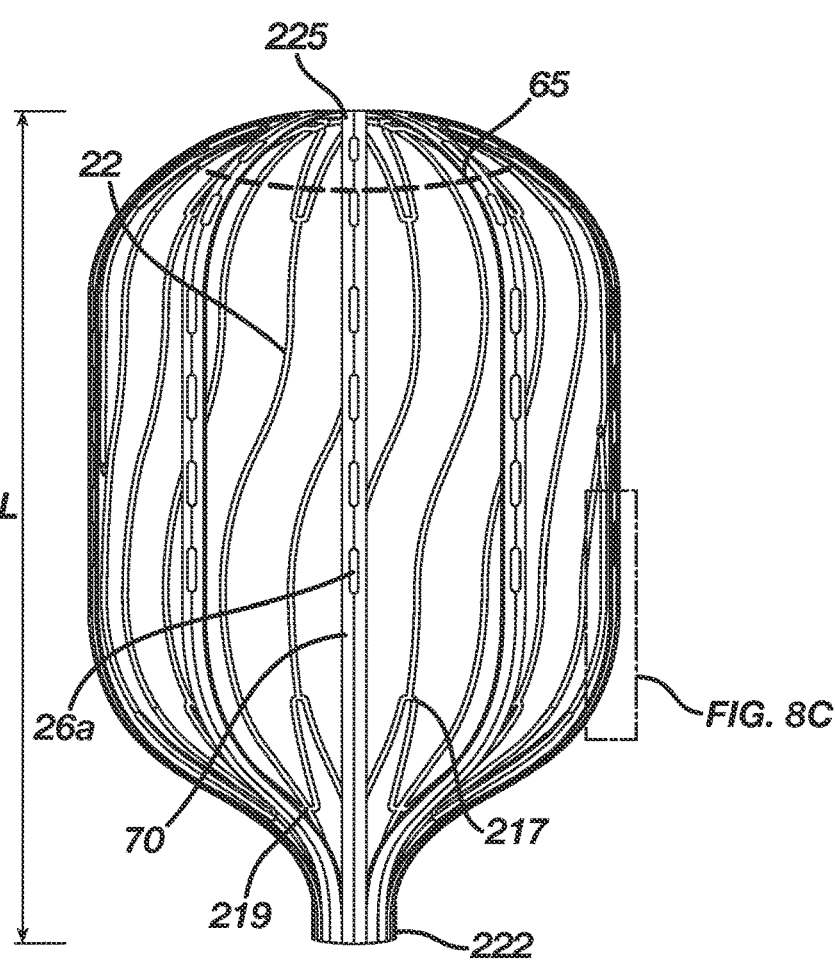
FIG. 8A
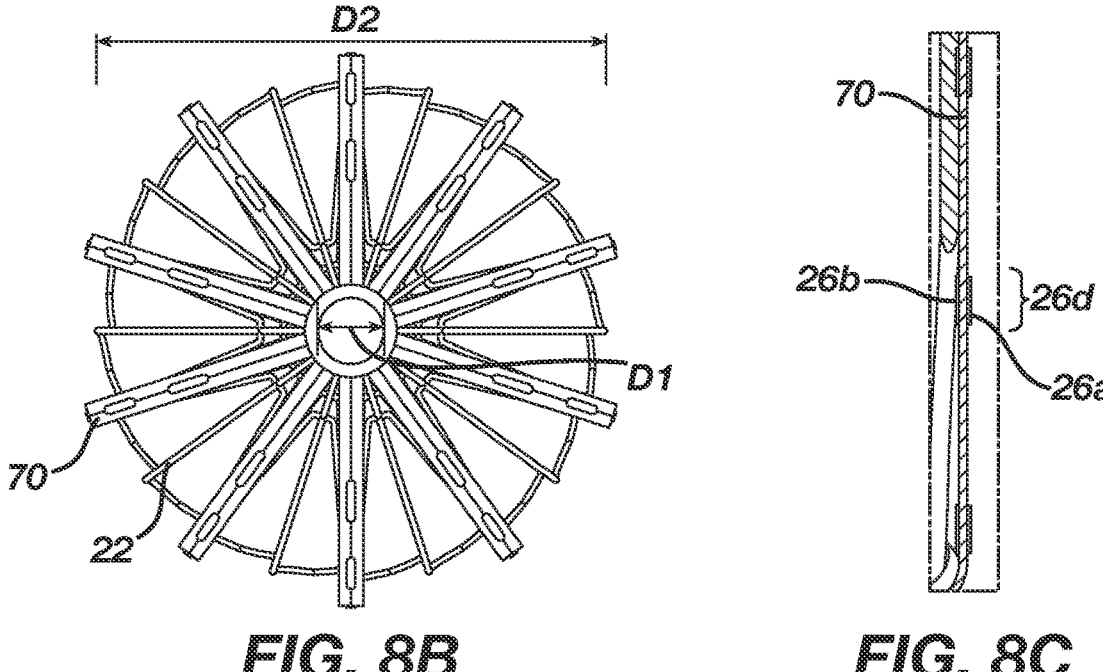
FIG. 8B          FIG. 8C

SYSTEMS AND METHODS FOR CYLINDRICAL CAGE MAPPING AND ABLATION CATHETERS HAVING FLEXIBLE CIRCUITS

CROSS REFERENCE TO RELATED APPLICATIONS

This application claims the benefit of priority under 35 U.S.C. § 119 to prior filed U.S. Provisional Patent Application No. 63/477,754, filed Dec. 29, 2022, the entire contents of which is hereby incorporated by reference as if set forth in full herein.

FIELD

The present invention relates generally to medical devices, and in particular catheters with electrodes, and further relates to, but not exclusively, catheters suitable for use for mapping, ablation, or to induce irreversible electroporation (IRE) of cardiac tissues and the pulmonary vein.

BACKGROUND

Electrophysiology catheters are commonly used for mapping electrical activity of the heart or inducing ablation to regions of cardiac tissue to cease or modify the propagation of unwanted electrical signals from one portion of the heart to another. Many electrophysiology catheters have a basket-shaped electrode arrays. In particular, catheters having basket-shaped electrode arrays are known and described, for example, in U.S. Pat. Nos. 5,772,590, 6,748,255 and 6,973,340, each of which are incorporated herein by reference and attached in the appendix to priority application U.S. 63/477,754. Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of ablation or irreversible electroporation (IRE) energy to tissues using multi-electrode catheters was previously proposed in the patent literature. Examples of systems and devices configured for IRE ablation are disclosed in U.S. Patent Pub. Nos. 2021/0169550A1 (now U.S. Pat. No. 11,660,135), 2021/0169567A1, 2021/0169568A1, 2021/0161592A1 (now U.S. Pat. No. 11,540,877), 2021/0196372A1, 2021/0177503A1, and 2021/0186604A1 (now U.S. Pat. No. 11,707,320), each of which are incorporated herein by reference and attached in the appendix to priority application U.S. 63/477,754.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. A spherical basket assembly is capable of detecting the electrical function of the left or right atrium. However, because the pulmonary veins are typically not perfectly round but or more oval in cross section, a substantially cylindrical assembly having a planar array of electrodes may provide a more uniform detection of the electrical function of the cardiac tissue at or near the pulmonary vein. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved medical probe that can help to reduce the time required for manufacturing and alternative catheter geometries in general.

SUMMARY

Various embodiments of a medical probe and related methods are described and illustrated. The present disclosure includes a medical probe may include a substantially cylindrical structure. The substantially cylindrical structure can include a proximal circular base, a distal circular base substantially parallel to the proximal circular base, a plurality of spines extending along a longitudinal axis between the proximal circular base and the distal circular base, and one or more strips of flexible circuit substrate coupled to one or more of the plurality of spines. Each spine can include a trifurcation point positioned along at least a portion of the spine, and a spine branch extending from the trifurcation point further comprising a bifurcation point.

The present disclosure includes a method of constructing a medical probe. The method can include fabricating a flexible circuit substrate into one or more strips; positioning the one or more strips over a substantially cylindrical structure comprising a plurality of spines; and configuring the plurality of spines to extend radially outward from a tubular configuration along a longitudinal axis to define a substantially cylindrical structure.

BRIEF DESCRIPTION OF THE DRAWINGS

FIG. 8A is a schematic pictorial illustration showing a side view of a substantially cylindrical structure with a sinusoidal cage in an expanded form, in accordance with an embodiment of the present invention;

FIG. 8B is a schematic pictorial illustration showing a top view of a substantially cylindrical structure with a sinusoidal cage in an expanded form, in accordance with an embodiment of the present invention;

FIG. 8C is a schematic pictorial illustration showing a cross-sectional view of a strip of flexible circuit substrate of FIG. 8A with electrodes embedded on an external surface and an internal surface, in accordance with an embodiment of the present invention;

DETAILED DESCRIPTION

Figure 1:
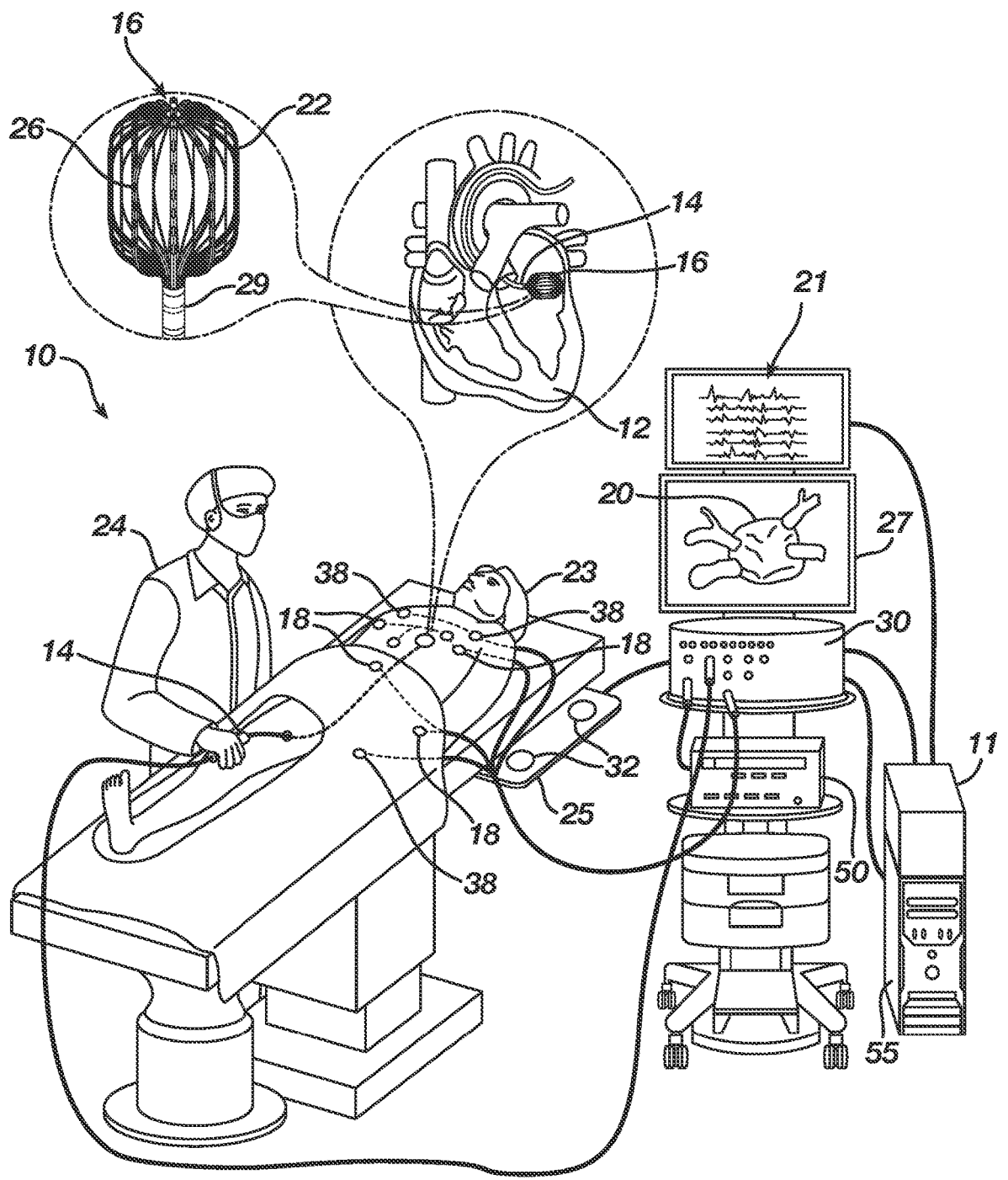
FIG. 1 is a schematic pictorial illustration of a medical system including a medical probe whose distal end includes a substantially cylindrical structure with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 110%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "physician" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode including a high current density and high electric flux density is positioned at a treatment site, and a second electrode including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating." as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to a membrane positioned over spines. Example systems, methods, and devices of the present disclosure may be particularly suited for mapping and IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the appendix to priority application U.S. 63/477,754.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications Nos. 2021/0169550A1 (now U.S. Pat. No. 11,660,135), 2021/0169567A1, 2021/0169568A1, 2021/0161592A1 (now U.S. Pat. No. 11,540,877), 2021/0196372A1, 2021/0177503A1, and 2021/0186604A1 (now U.S. Pat. No. 11,707,320), the entireties of each of which are incorporated herein by reference and attached in the appendix to priority application U.S. 63/477,754.

To deliver pulsed field ablation (PFA) in an IRE (irreversible electroporation) procedure, electrodes should contact the tissue being ablated with a sufficiently large surface area. As described hereinbelow, the medical probe includes a substantially cylindrical structure having a proximal circular base, a distal circular base substantially parallel to the proximal circular base, a plurality of spines extending along a longitudinal axis between the proximal circular base and the distal circular base, and one or more strips of flexible circuit substrate coupled to one or more of the plurality of spines defining an internal volume about the longitudinal axis. The plurality of spines include a trifurcation point positioned along at least a portion of the spine and a spine branch extending from the trifurcation point further comprising a bifurcation point. The one or more strips of flexible circuit substrate further include one or more conductive traces disposed on a surface of the substrate. The strips of flexible circuit substrate further include one or more reference electrodes coupled to an internal surface of the substrate such that the reference electrodes are co-located with respective electrodes on the external surface to define a stacked pair of electrodes Reference is made to FIG. 1, showing an example catheter-based electrophysiology mapping and ablation system 10. System 10 includes multiple catheters, which are percutaneously inserted by physician 24 through the patient's 23 vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician 24 brings a distal tip 28 of catheter 14 comprising a medical probe 16 into contact with the heart wall at or near the pulmonary vein for sensing a target site in heart 12. For ablation, physician 24 would similarly bring a distal end of an ablation catheter comprising medical probe 16 to a target site for ablating.

Medical probe 16 is an exemplary probe that includes one and preferably multiple electrodes 26 optionally distributed over a plurality of spines 22 at distal tip 28 and configured to sense the IEGM signals. Medical probe 16 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation. As shown in more detail in FIG. 2A, medical probe 16 can include a one or more strips of flexible circuit substrate 70 positioned over the plurality of spines 22 and coupled to at least a portion of some individual spines 220. Position sensor 29 can be conventional coiled wire sensors, flat PCB based sensors, or deformable electromagnetic loop sensors. Although not depicted, position sensor 29 can alternatively be positioned on the basket assembly 28 or designed into individual spines 22. In some embodiments, individual spines 22 can be insulated and act as a position sensor.

In some embodiments, medical probe 16 can include a deformable electromagnetic loop sensor Examples of various systems and methods for deformable electromagnetic loop sensors are presented in U.S. Pat. Nos. 11,304,642 and 10,330,742, and U.S. Patent Publications 2018/0344202A1 and 2020/0155224A1, each of which are incorporated herein by reference and attached in the appendix to priority application U.S. 63/477,754.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091, each of which are incorporated herein by reference and attached in the appendix to priority application U.S. 63/477,754.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182, each of which are incorporated herein by reference and attached in the appendix to priority application U.S. 63/477,754.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618 USA.

Figures 2A, 2B:
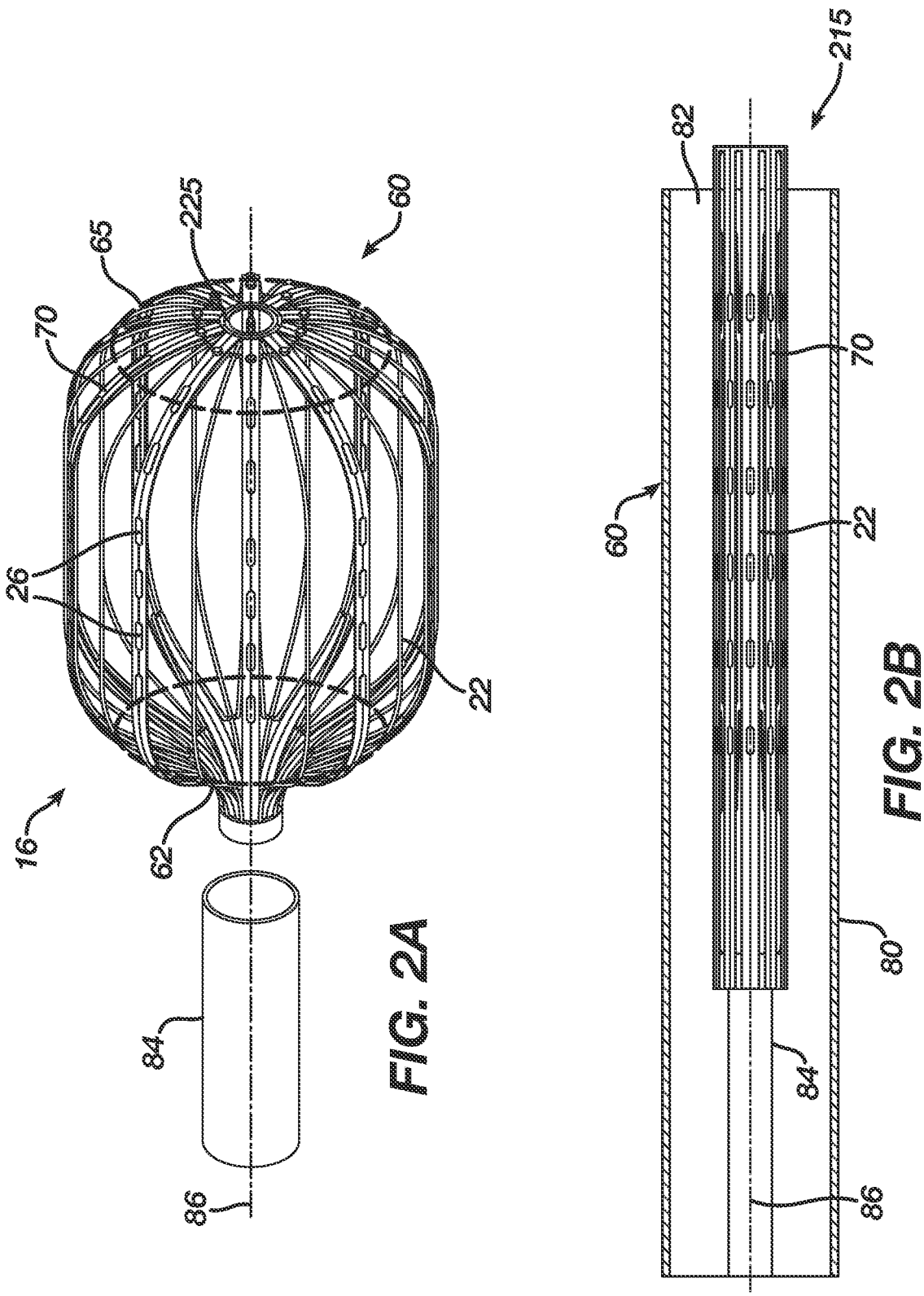
FIG. 2A is a schematic pictorial illustration showing a perspective view of a medical probe in an expanded form, in accordance with an embodiment of the present invention.
FIG. 2B is a schematic pictorial illustration showing a side view of a medical probe in a collapsed form, in accordance with embodiments of the present invention.

FIG. 2A is a schematic pictorial illustration showing a perspective view of medical probe 16 including a substantially cylindrical structure 60 in an expanded form when unconstrained, such as by being advanced out of an insertion tube lumen 82 at a distal end 83 of an insertion tube 80. The medical probe 16 illustrated in FIG. 2A lacks the guide sheath illustrated in FIG. 1. FIG. 2B shows the substantially cylindrical structure 60 in a collapsed form within insertion tube 80 of the guide sheath. During a medical procedure, physician 24 can deploy cylindrical structure 60 by extending tubular shaft 84 from insertion tube 80, causing cylindrical structure 60 to exit insertion tube 80 and transition to the expanded form.

Each spine 220 of the plurality of spines 22 may have elliptical (e.g., circular) or rectangular (that may appear to be flat) cross-sections, and include a flexible, resilient material (e.g., a shape-memory alloy such as nickel-titanium, also known as Nitinol) forming a spine as will be described in greater detail herein. The spines 220 may have a nominal width of approximately 0.6 mm and can be as low as 0.2 mm or as large as 1.5 mm. The thickness of each spine can be nominally 0.09 mm and can vary from 0.05 mm to 0.2 mm. It should be noted that these values for width and thickness can vary depending on the stiffness desired.

As shown in FIG. 2A, the substantially cylindrical structure 60 includes a proximal circular base 62 and a distal circular base 65 such that the proximal base 62 and distal base 65 are substantially planar and parallel. In some examples, the distal circular base 65 includes a radius smaller than the proximal circular base 62 such that the substantially cylindrical structure 60 is tapered with a larger proximal portion than distal portion. Alternatively, some example medical probes 16 have a substantially cylindrical structure 60 with a larger radius at the distal circular base 65 than the proximal circular base 62 such that the substantially cylindrical structure 60 is tapered with a larger distal portion than proximal portion. As shown, the radii of the distal circular base 65 is similar to the proximal circular base 62.

In some embodiments, cylindrical structure 60 further includes one or more strips of flexible circuit substrate 70 positioned over the plurality of spines 22. Circuit substrate 70 and plurality of spines 22 defines an internal volume 66 within substantially cylindrical structure 60. Strips of flexible circuit substrate 70 allows fluid to enter into the internal volume 66 such that a fluid communication exists between the outside the circuit substrate 70 and the internal volume 66. As shown, strips of flexible circuit substrate 70 include electrodes 26 positioned on the surface of the circuit substrate 70.

Figures 3A, 3B:
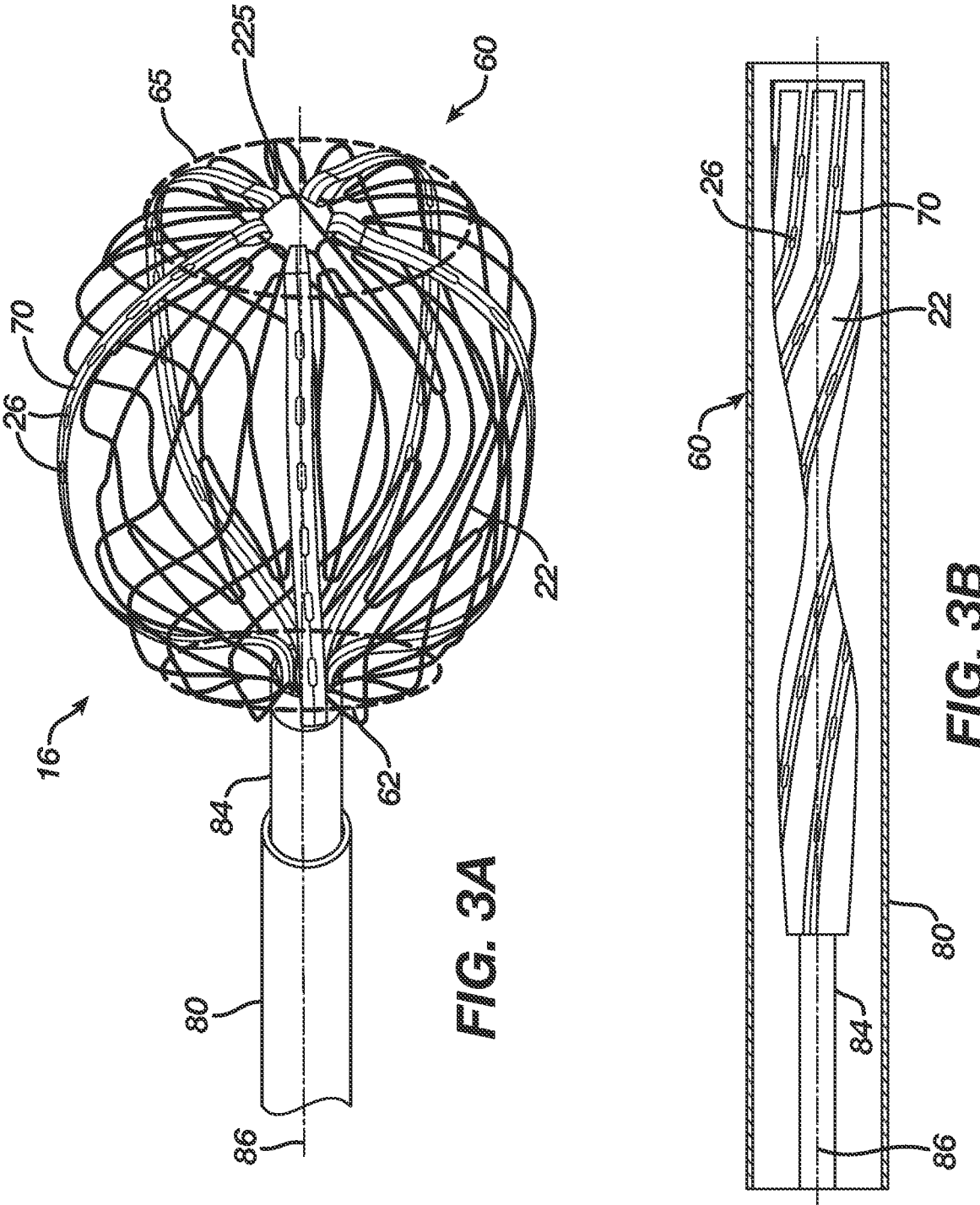
FIG. 3A is a schematic pictorial illustration showing a perspective view of a medical probe with a sinusoidal cage in an expanded form, in accordance with an embodiment of the present invention.
FIG. 3B is a schematic pictorial illustration showing a side view of a medical probe with a sinusoidal cage in a collapsed form, in accordance with embodiments of the present invention.

FIG. 3A is a schematic pictorial illustration showing an example medical probe 16 having a substantially cylindrical structure 60 with a plurality of spines 22 running approximately sinusoidal along the longitudinal axis 86 when in the expanded form. The one or more strips of flexible circuit substrate 70 can be linear in shape and coupled to at least a portion of one or more spines 220. When in the collapsed form, such as when constrained against the walls of the insertion tube 80, the sinusoidal spines can twist along a portion of the middle, as shown in FIG. 3B. During a medical procedure, physician 24 can deploy cylindrical structure 60 by extending tubular shaft 84 from insertion tube 80, causing cylindrical structure 60 to exit insertion tube 80, untwist, and transition to the expanded form.

Figure 4A:
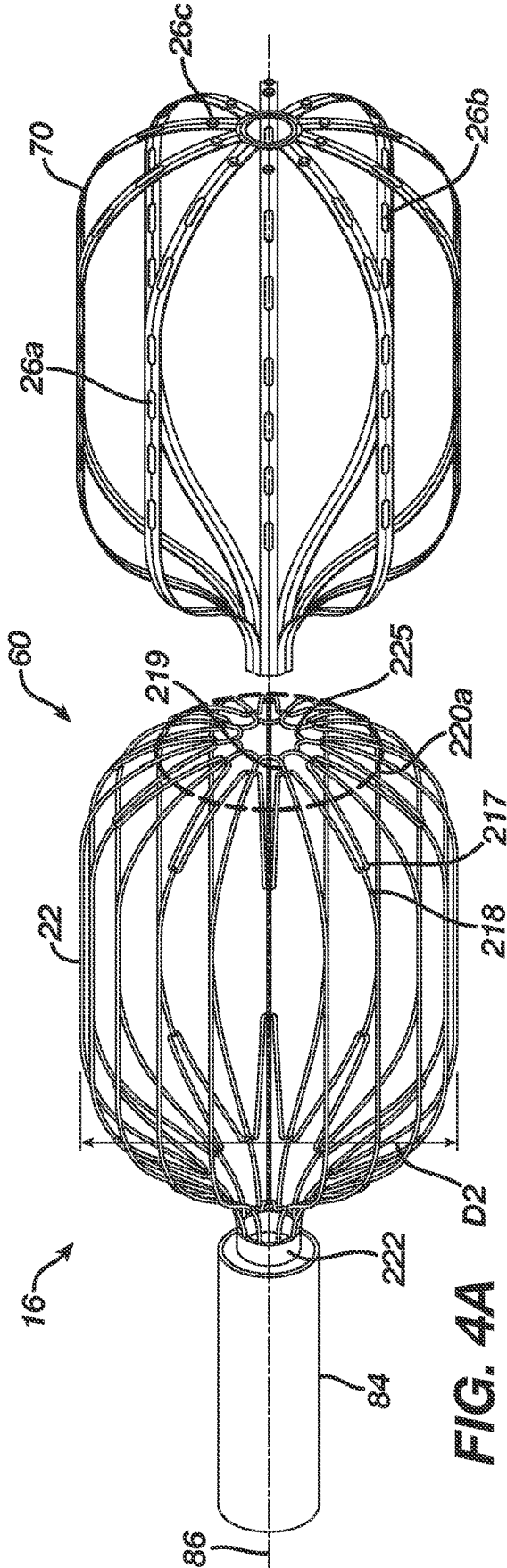
FIG. 4A is a schematic pictorial illustration showing an exploded side view of a medical probe, in accordance with an embodiment of the present invention.

FIG. 4A is an exploded side view of medical probe 16, showing one or more strips of flexible circuit substrate 70 having an array of electrodes including external electrodes 26a, internal or reference electrodes 26b, and mapping electrodes 26c on the substantially planar surfaces. As illustrated in FIGS. 2A and 3A, the strips of flexible circuit substrate 70 fit over the plurality of spines 22 that expand into a substantially cylindrical shape. The substantially cylindrical structure 60 can be physically connected to the tubular member 84 via a suitable technique such as adhesive or molding. In one embodiment not shown, eyelets can be provided along the proximal ring 222 as well as locators on a surface of the tubular member 84 to aid in assembly as well as physical retention of the spines to the tubular member 84.

The plurality of spines 22 can be folded or otherwise bent such that each spine 220 or the proximal ring 222 can be inserted into the distal end 85 of the tubular shaft 84 (as shown in FIG. 4A). Although not shown in FIG. 3, it will be appreciated that electrodes 26 can be attached into strips of flexible circuit substrate 70 before the circuit substrate 70 is positioned over the plurality of spines 22 and the spines 22 are inserted into the tubular shaft 84 to form the medical probe 16. As stated previously, the spines 22 can include a flexible, resilient material (e.g., a shape-memory alloy such as nickel-titanium, also known as Nitinol) that can enable the substantially cylindrical structure 60 to transition to its expanded form when substantially cylindrical structure 60 is deployed from tubular shaft 84.

Figure 4B:
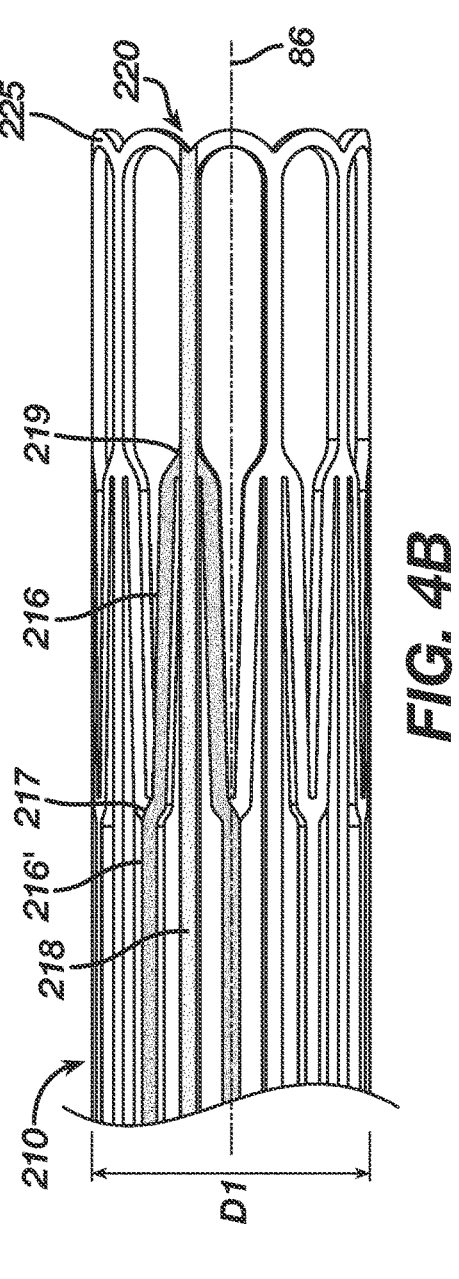
FIG. 4B is a schematic pictorial illustration showing a side view of a bifurcation design in a hollow tube, in accordance with embodiments of the present invention.

Turning to FIG. 4B, the spine assembly can be made from a hollow tubular cylindrical stock material 210 so that a proximal ring 222 and distal ring 225 are of one-piece material. The tubular stock 210 is cut into a desired shape for the spine assembly as shown in FIG. 4A. Thereafter, the cut tube 210 can be shape set (or heat set) as is known by those skilled in the art to provide for the substantially cylindrical configuration shown in FIG. 4A. As shown, hollow tube 210 has a first diameter D1 approximately uniform along the length of hollow tube 210, but when unconstrained, the cylindrical structure 60 expands to a second diameter D2 shown in FIG. 4A. The distal ring 225 and proximal ring 220 of the cylindrical structure maintains the first diameter D1 of the hollow tube 210. In some embodiments, the diameter of the cylindrical structure in the expanded form can be about 15 mm±5 mm.

In some embodiments described herein, and shown in FIG. 4B, each spine 220 of the plurality of spines 22 includes a trifurcation point 219 and a bifurcation point 217 positioned along at least a portion of the spine. One of the trifurcation point 219 or bifurcated point 217 can be positioned along at least a portion of the spine between the distal circular base 65 and the proximal circular base 62. As one example, FIG. 4A shows the trifurcation point 219 within the distal circular base 65 while the bifurcation point 217 is positioned between the distal circular base 65 and the proximal circular base 62. Each spine 220 of the plurality of spines 22 also includes a first spine branch 216 between the trifurcation point 219 to the bifurcation point 216. Each spine 220 may also include a second spine branch 216' positioned after the trifurcation point 219. At the trifurcation point 219, the spine is maintained in the middle and forms a middle portion 218 extending between the distal circular base 65 and the proximal circular base 62 and is the outer most portion when the cylindrical structure 60 is in the expanded form. In some example medical probes 16, the cylindrical structure 60 has a length ranging from about 10 mm to about 20 mm between the distal circular base 65 and the proximal circular base 62. Preferably, the length L of the cylindrical structure 60 between the proximal end 212 and the distal end 215 is approximately 15 mm.

In some embodiments, the plurality of spines 22 can optionally only have a bifurcation point. For example, the hollow tube 210 of FIG. 4B could replace the trifurcation point 219 with a second bifurcation point 217. In such an example, the second spine branch 216' would become the middle portion 218.

Figure 5:
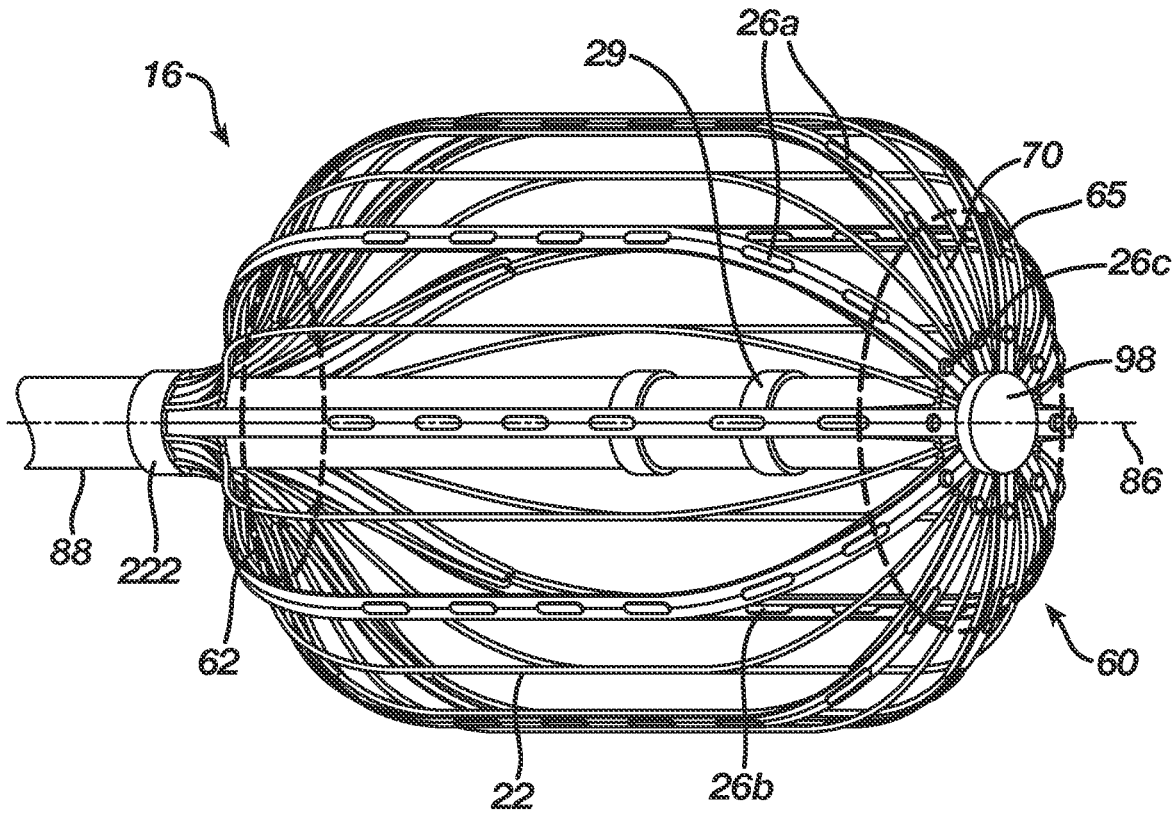
FIG. 5 is a schematic pictorial illustration showing a side view of a medical probe with a pusher tube in an expanded form, in accordance with embodiments of the present invention.

FIG. 5 is a schematic pictorial illustration showing a side view of a medical probe 16 having a substantially cylindrical structure 60 with a plurality of spines 22, one or more strips of flexible circuit substrate 70, and a pusher rod 88. As shown, pusher rod 88 can fit within proximal ring 222 and move within the internal volume 66 of the cylindrical structure 60 along the longitudinal axis 86. Pusher rod 88 can also include position sensor 29 embedded in or near a distal tip 28 for tracking position and orientation of medical probe 16 in the expanded configuration. As shown, flexible circuit substrate 70 can include outward-facing electrodes 26a, internal-facing electrodes 26b, and mapping electrodes 26c. Mapping electrodes 26c can be conventional coiled wire sensors, flat PCB based sensors, or deformable electromagnetic loop sensors. Although not depicted, mapping electrodes 26c can alternatively be positioned on the substantially cylindrical structure 60 or designed into individual spines of the plurality of spines 22.

The reference electrodes can be configured to measure the electrical signals from the fluid and/or blood directly adjacent to an electrode that is touching tissue. As such, the reference electrodes are insulated from touching tissue and the resulting signals collected are non-local far-field signals. The information from this reference electrode can be used to cancel out far-field signal from the adjacent, tissue touching electrode to ensure that the tissue touching electrode collects local information only.

In some embodiments, individual spines 220 of the plurality of spines 22 can be insulated and act as a position sensor. In some embodiments, pusher rod 88 may include an ablation electrode 98 at the distal tip 28 that fits through the distal ring 225 of the substantially cylindrical structure 60.

Figure 6A:
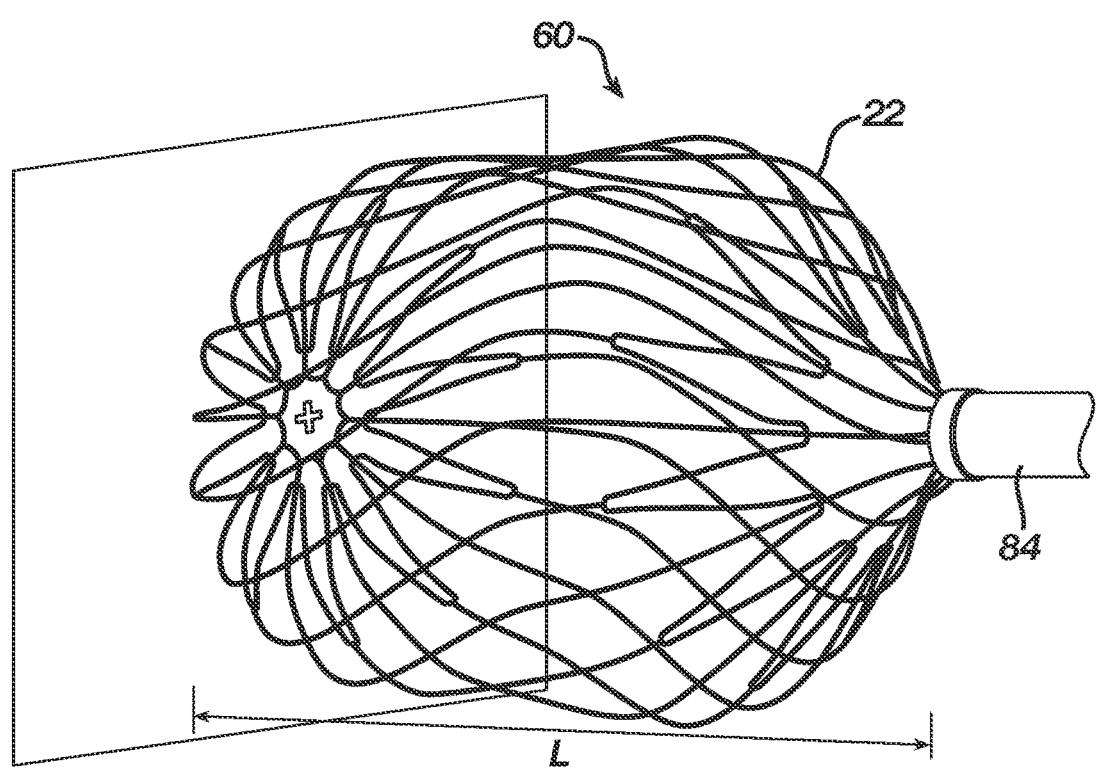
FIGS. 6A and 6B are schematic pictorial illustrations showing side views of a plurality of spines compressing when in contact with a surface, in accordance with embodiments of the present invention.
Figure 6B:
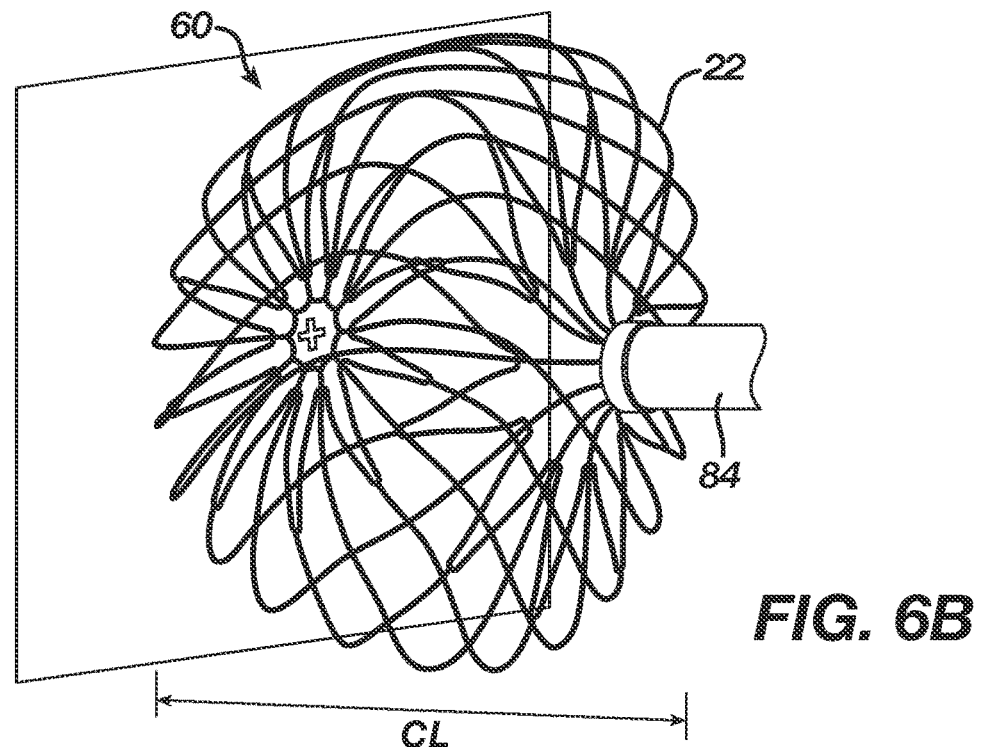

FIGS. 6A and 6B are schematic pictorial illustrations showing side-views of the plurality of spines 22, cut from the hollow tube 210, as described supra, and compressing due to a force of contacting a target. The plurality of spines 22 expand to an unconstrained length L, that compress to a compressed length CL and flexibly move the substantially cylindrical structure 60 due to the trifurcation and bifurcation of the plurality of spines 22. As would be appreciated by one of skill in the art, positioning a bifurcation or trifurcation at different locations along the longitudinal axis 86 of the cylindrical structure 60 can alter the flexibility of the cylindrical structure 60 or may allow for different membrane and/or electrode array designs for the medical probe 16.

Figure 7A:
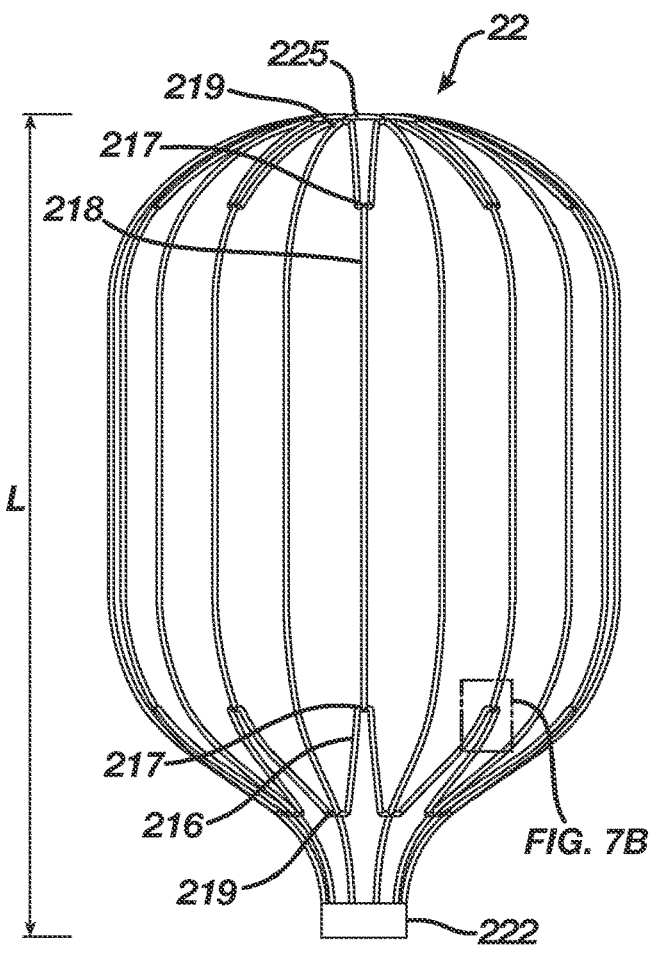
FIG. 7A is a schematic pictorial illustration showing a side view of a plurality of spines forming a substantially cylindrical structure, in accordance with an embodiment of the present invention.
Figure 7B:
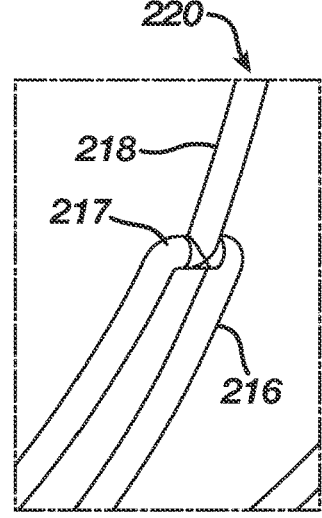
FIG. 7B is a schematic pictorial illustration of a bifurcation point along the substantially cylindrical structure of FIG. 7A, in accordance with an embodiment of the present invention.
Figure 7C:
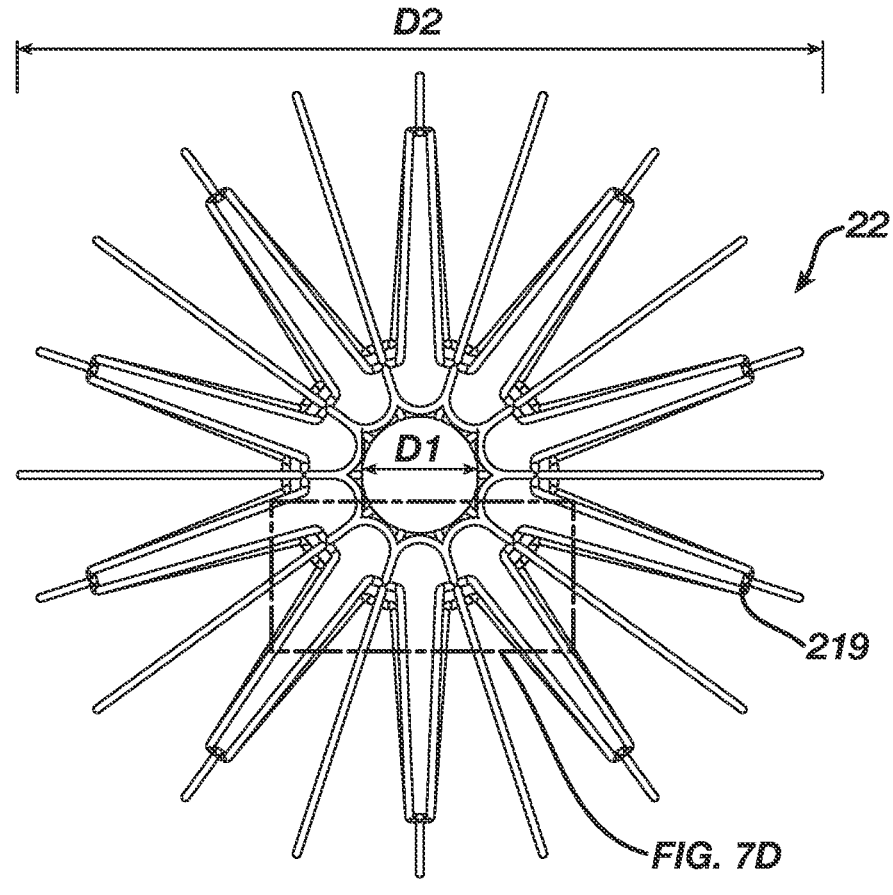
FIG. 7C is a schematic pictorial illustration showing a top view of a plurality of spines forming a substantially cylindrical structure, in accordance with an embodiment of the present invention.
Figure 7D:
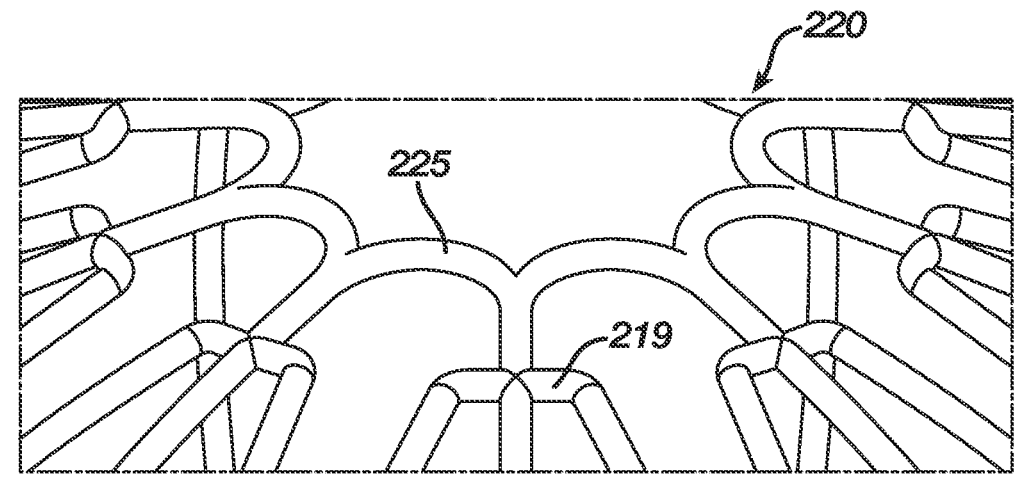
FIG. 7D is a schematic pictorial illustration of a trifurcation point along the substantially cylindrical structure of FIG. 7C, in accordance with an embodiment of the present invention.

FIG. 7A is a schematic pictorial illustration showing a side view of a plurality of spines 22 having both a bifurcation point 217 and a trifurcation point 219. The plurality of spines 22 expand to an unconstrained length L between the proximal ring 222 and distal ring 225, that when compressed due to a force of contacting a tissue such as the heart, the plurality of spines 22 can flexibly move due to the bifurcation and trifurcation. In the expanded form, the proximal ring 222 and the distal ring 225 of the plurality of spines 22 has a first diameter D1 that, as described supra, is substantially equal to the diameter of the hollow tube. In the expanded form, the plurality of spines 22 expands to a second diameter D2. As shown in FIG. 7B, a close-up image of an individual spine shows a middle portion 218, a bifurcation point 217, and two spine branches 216. FIG. 7C shows a top view of the plurality of spines 22 expanded to the second diameter D2, and the trifurcation points 219, one of which is shown close-up in FIG. 7D.

FIGS. 8A and 8B are schematic pictorial illustrations showing a side view and a top view of another trifurcation design of the plurality of spines 22 with a curve along the middle portion 218 with respect to the longitudinal axis 86. As shown, the spines can be sinusoidal, but the design can also be a suitable curvilinear such that the plurality of spines 22 twists when transitioning from the collapsed form (FIG. 3B) to the expanded form as shown in FIG. 8B. The plurality of spines 22 expand to an unconstrained length L, that when compressed due to a force of contacting a tissue such as the heart, the plurality of spines 22 can flexibly move due to the design of the spines.

FIG. 8C a schematic pictorial illustration showing a cross-sectional view of the membrane of FIG. 8A with electrodes embedded on an external surface and an internal surface. In some embodiments, the external-facing electrodes 26a and internal-facing electrode 26b form stacked electrodes 26d in that they are aligned on opposing sides of the strips of flexible circuit substrate 70 as shown in FIG. 8C.

Figures 9A, 9B, 9C, 9D:
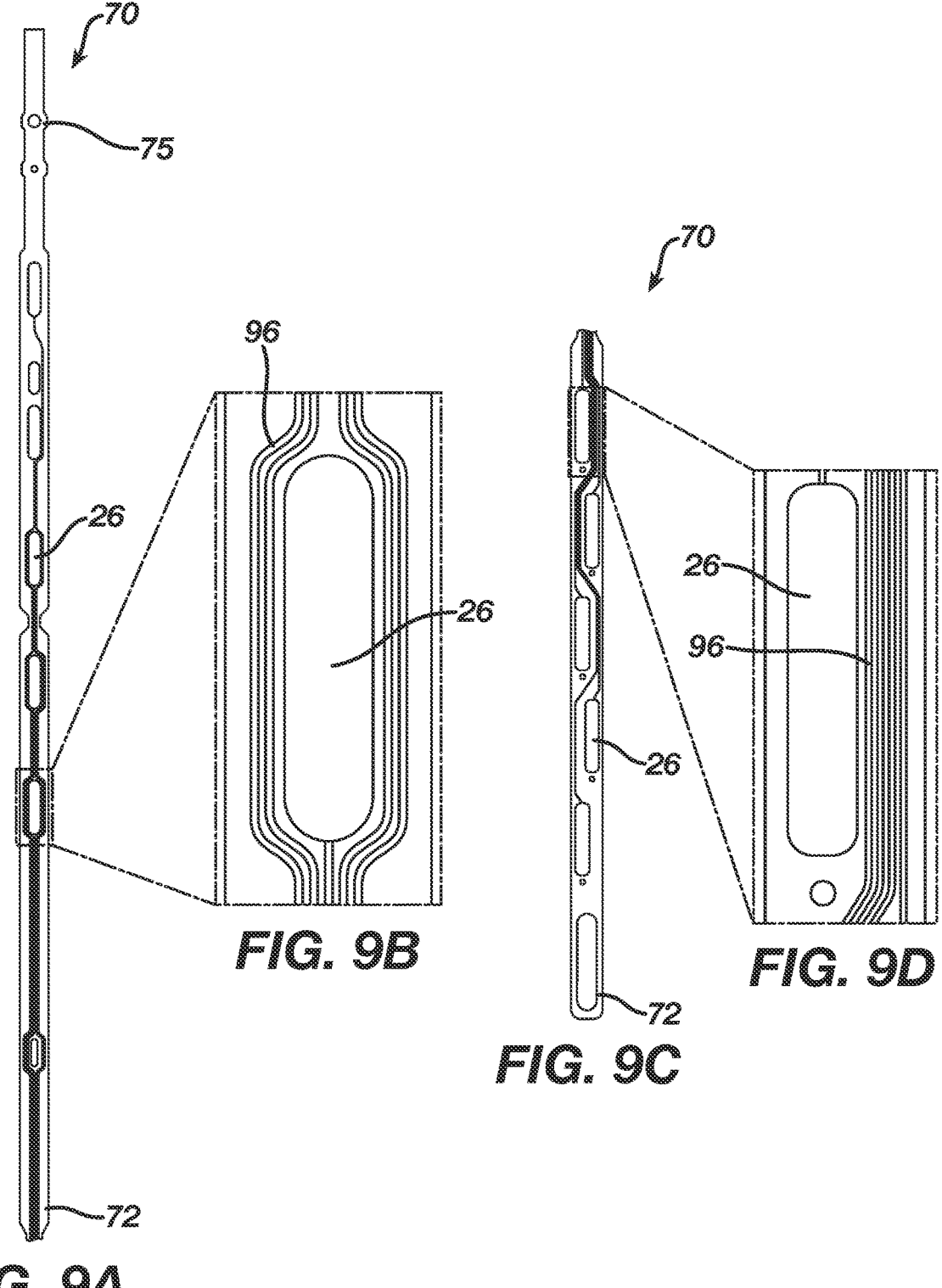
FIGS. 9A through 9D are schematic pictorial illustration showing the strips of flexible circuit substrate with electrodes and electrical traces, in accordance with an embodiment of the present invention.

FIGS. 9A through 9D are schematic pictorial illustration showing the strips of flexible circuit substrate 70 with electrodes 26 and electrical traces 96. In some embodiments, electrical traces 96 are embedded within the circuit substrate and shown as lines connecting the one or more electrodes 26 that are coupled to an external surface of the flexible circuit substrate 70, as shown in FIGS. 9A and 9C. Shown in more detail in FIG. 8C, electrodes 26 are disposed on the flexible circuit substrate 70 external surface and on the flexible circuit substrate 70 internal surface such that the electrodes define a stacked pair of electrodes 26d. Electrodes 26b disposed on the flexible circuit substrate internal surface can function as reference electrodes. The reference electrodes can measure electrical signals from the fluid in the internal volume 66 of the medical probe 16 to reduce noise, improve accuracy of mapping, and the like.

In embodiments described herein, one or more electrodes 26 positioned on the flexible circuit substrate 70 of the cylindrical structure 60 can be configured to deliver ablation energy (RF and/or IRE) to tissue in heart 26. The plurality of spines 22 can be electrically isolated from electrodes 26 to prevent arcing from electrodes 26 to the respective spine 220. Additionally, the electrodes can also be used to determine the location of the medical probe 16 and/or to measure a physiological property such as local surface electrical potentials at respective locations on tissue in heart 26. The electrodes 26 can be biased such that a greater portion of the one or more electrodes 26a face outwardly from the substantially cylindrical structure 60 such that the one or more electrodes 26a deliver a greater amount of electrical energy outwardly away from the cylindrical structure 60 (i.e., toward the heart 12 tissue) than inwardly.

Examples of materials ideally suited for forming electrodes 26 include gold, platinum and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 12.

As described supra, PIU 30 and workstation 55 includes controls for irrigation that delivers irrigation fluid to the medical probe 16. Although not depicted, multiple irrigation openings can be positioned within the internal volume 66 of the substantially cylindrical structure 60 and angled to spray or otherwise disperse of the irrigation fluid to either a given electrode 26 or to tissue in heart 12. Since electrodes 26 do not include irrigation openings that deliver irrigation fluid, the configuration described enables heat to be transferred from the tissue (i.e., during an ablation procedure) to the portion of the electrodes on the inner side of the plurality of spines 22, and the electrodes 26 can be cooled by aiming the irrigation fluid, via irrigation openings, at the portion of the electrodes 26 on the inner side of the spines 22.

The flexible circuit substrate 70 can include multiple proximal attachment points 72 and distal attachment points 75 (as shown in FIG. 9A). Although not shown, membrane 70 can be designed from a planar material with the distal attachment point 75 central and the material extending proximally along the longitudinal axis 86. Flexible circuit substrate 70 can be made from a biocompatible, electrically insulative material such as polyamide-polyether (Pebax) copolymers, polyethylene terephthalate (PET), urethanes, polyimide, parylene, silicone, and combinations thereof. In some examples, insulative material can include biocompatible polymers including, without limitation, polyethylbenzene, polydimethylsiloxane, polyglycolic acid, poly-L-lactic acid, polycaprolactive, polyhydroxybutyrate, polyhydroxyvalerate, polydioxanone, polyamides, polyimides, ethylene vinyl acetates, polyvinylidene fluoride, polycarbonate, polypropylene, polyethylene, polyurethanc, polyethylene terephthalate, polyethylene naphthalate, polyanhydride, polycaprolactone, polydioxanone, polybutyrolactone, polyvalerolactone, poly(lactide-co-glycolide), polydimethylsiloxane, silicone, epoxy, fluoropolymer, polytetrafluoroethylene, with the ratio of certain polymers being selected to control the degree of inflammatory response. Flexible circuit substrate 70 can help to insulate the plurality of spines 22, electrical traces 96, or wires passing through flexible circuit substrate 70 from electrodes 26 to prevent arcing from electrodes 26 to the spines 22 and/or mechanical abrasion of wires passing through flexible circuit substrate 70.

Figure 10:
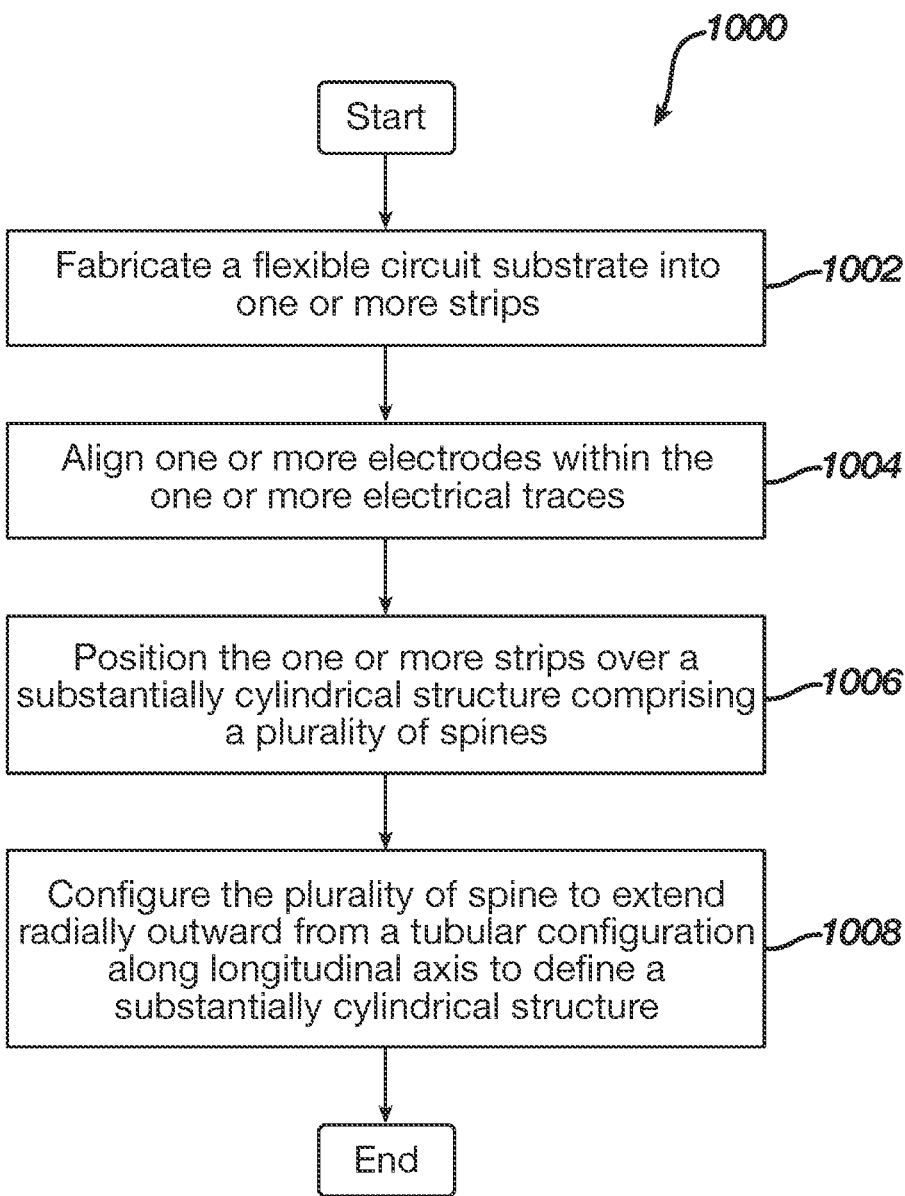
FIG. 10 is a flowchart illustrating another method of assembling a medical probe having a substantially cylindrical structure, in accordance with an embodiment of the present invention.

FIG. 10 is a flowchart illustrating a method 1000 of manufacturing a medical probe 16, in accordance with an embodiment of the present invention. Method 1000 can include fabricating a flexible circuit substrate 70 into one or more strips (step 1002). Fabricating electrical traces can be completed prior to or simultaneously with aligning one or more electrodes 26 within the one or more electrical traces 96 on the flexible circuit substrate 70 (step 1004). Flexible circuit substrate 70 may include an array of electrodes including external-facing (with respect to the medical probe) electrodes 26a, internal-facing or reference electrodes 26b, and mapping electrodes 26c. The electrodes can be positioned such that the electrodes 26 are offset from neighboring electrodes 26 along the flexible circuit substrate 70 or neighboring strips of flexible circuit substrate 70. Alternatively, electrodes 26 can be aligned within a linear array that is substantially equal to neighboring strips flexible circuit substrate 70. Materials ideally suited for forming electrodes 26 include gold, platinum and palladium (and their respective alloys). Flexible circuit substrate 70 can be cut from a planar resilient material. The planar resilient material can include shape-memory alloy such as nickel-titanium (also known as Nitinol) or a biocompatible polymer including, without limitation, polyethylbenzene, polydimethylsiloxane, polyglycolic acid, poly-L-lactic acid, polycaprolactive, polyhydroxybutyrate, polyhydroxyvalerate, polydioxanone, polyamides, polyimides, ethylene vinyl acetates, polyvinylidene fluoride, polycarbonate, polypropylene, polyethylene, polyurethane, polyethylene terephthalate, polyethylene naphthalate, polyanhydride, polycaprolactone, polydioxanone, polybutyrolactone, polyvalerolactone, poly (lactide-co-glycolide), polydimethylsiloxane, silicone, epoxy, fluoropolymer, polytetrafluoroethylene, or combinations thereof. In some examples, method 1000 can develop the membrane by vapor deposition (e.g., chemical vapor deposition (CVD, physical vapor deposition (PVD), or atomic layer deposition (ALD)). For vapor deposition, a layer of nitinol can be deposited, followed by a thin insulation layer, and then the conductive trace and electrode layers. In some examples, method 1000 can develop the membrane by lithography methods, sputtering methods (e.g., spin coating, direct-write sputtering, or sputter coating), printing (e.g., 3D printing), electrodeposition, photolithography.

Method 1000 further includes positioning the one or more strips of flexible circuit substrate 70 over a substantially cylindrical structure 60 comprising a plurality of spines 22 (step 1006). The strips of flexible circuit substrate 70 can be fastened over the plurality of spines 22 as described herein. As will be appreciated by one of skill in the art including the benefit of this disclosure, fastening the strips of flexible circuit substrate 70 can include attaching the proximal attachment point(s) 72 to the proximal ring 222 of the plurality of spines 22 or to the tubular shaft 84. Method 1000 can include configuring the plurality of spines 22 to extend radially outward from a longitudinal axis 86 to define the substantially cylindrical structure 60 (step 1008). Configuring the plurality of spines 22 to extend radially outward can include cutting a design, from a hollow tube 210, for form spines that are shape set (or heat set) to provide the substantially cylindrical structure 60. The hollow tube 210 can include shape-memory alloy such as nickel-titanium (also known as Nitinol), cobalt chromium, or any other suitable material. As described supra, the plurality of spines 22 includes bifurcation and/or trifurcation along at least a portion of the spine 210.

In some examples, steps 1002 through 1008 may occur as simultaneous steps or as a sequence of steps.

Method 1000 can include inserting each spine 210 or the proximal ring 222 into a lumen of a tubular shaft 84 sized to traverse vasculature such that the substantially cylindrical structure 60 is positioned at a distal end of the medical probe 16 and respective spines 220 are movable from a tubular configuration to a bowed configuration.

As will be appreciated by one skilled in the art, method 1000 can include any of the various features of the disclosed technology described herein and can be varied depending on the particular configuration. Thus, method 1000 should not be construed as limited to the particular steps and order of steps explicitly described herein. It is noted that while the preference for the exemplary embodiments of the medical probe is for mapping, IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

The disclosed technology described herein can be further understood according to the following clauses:

Clause 1: A medical probe, comprising: a substantially cylindrical structure comprising: a proximal circular base; a distal circular base substantially parallel to the proximal circular base, a plurality of spines extending along a longitudinal axis, joining the distal and proximal circular base, each spine comprising: a trifurcation point positioned along at least a portion of the spine, and a spine branch extending from the trifurcation point further comprising a bifurcation point; and one or more strips of flexible circuit substrate coupled to one or more of the plurality of spines.

Clause 2: The medical probe according to clause 1, each spine of the plurality of spines joined at a distal end of the substantially cylindrical structure.

Clause 3: The medical probe according to clause 1, the plurality of spines configured to move from a tubular configuration to an expanded cylindrical configuration.

Clause 4: The medical probe according to any of clauses 1-3, the substantially cylindrical structure comprising a substantially planar distal portion circular base.

Clause 5: The medical probe according to any of clauses 1-4, the substantially cylindrical structure comprising a middle portion between the distal circular base and the proximal circular base, the middle portion comprising a length ranging from about 10 mm to about 20 mm.

Clause 6: The medical probe according to any of clauses 1-5, wherein the plurality of spines run linear along the longitudinal axis.

Clause 7: The medical probe according to any of clauses 1-5, wherein the plurality of spines run sinusoidal along the longitudinal axis.

Clause 8: The medical probe according to any of clauses 1-7, each spine of the plurality of spines joined at a proximal end of the substantially cylindrical structure.

Clause 9: The medical probe according to any one of clauses 1-8, wherein the distal circular base comprises a smaller radius than the proximal circular base.

Clause 10: The medical probe according to any one of clauses 1-8, wherein the distal circular base comprises a larger radius than the proximal circular base.

Clause 11: The medical probe according to any one of clauses 1-8, wherein the distal circular base comprises a radius approximately equal to the proximal circular base.

Clause 12: The medical probe according to any one of clauses 1-11, each spine converging into a distal ring at a distal end of the substantially cylindrical structure and a proximal ring at the proximal end of the substantially cylindrical structure.

Clause 13: The medical probe according to any of clauses 1-12, the substantially cylindrical structure further comprising one or more electromagnetic location coils on one or more of the plurality of spines.

Clause 14: The medical probe according to any one of clauses 1-13, the one or more strips of flexible circuit substrate joined at a distal end of the substantially cylindrical structure.

Clause 15: The medical probe according to any one of clauses 1-13, the one or more strips of flexible circuit substrate joined at a proximal end of the substantially cylindrical structure.

Clause 16: The medical probe according to any of clauses 1-15, the one or more strips of flexible circuit substrate comprising at least four strips.

Clause 17: The medical probe according to any of clauses 1-16, the one or more strips of flexible circuit substrate comprising eight strips.

Clause 18: The medical probe according to any of clauses 1-17, the one or more strips of flexible circuit substrate further comprising one or more conductive traces disposed on a surface of the substrate.

Clause 19: The medical probe according to any one of clauses 1-18, the one or more strips of flexible circuit substrate formed from a planar material.

Clause 20: The medical probe according to any one of clauses 1-19, wherein the strips of flexible circuit substrate comprise one or more electrodes coupled to an external surface of the substrate.

Clause 21: The medical probe according to clause 20, the strips of flexible circuit substrate further comprising one or more reference electrodes coupled to an internal surface of the substrate such that the reference electrodes are co-located with respective electrodes on the external surface to define a stacked pair of electrodes.

Clause 22: The medical probe according to clause 20, the one or more electrodes configured to supply electrical signals so as to apply a therapeutic procedure to a tissue with which the one or more electrodes are in contact.

Clause 23: The medical probe according to any one of clauses 1-22, wherein the one or more electrodes are configured to deliver electrical pulses for irreversible electroporation, the pulses having a peak voltage of at least 900 volts.

Clause 24: The medical probe according to any one of clauses 1-23, wherein the one or more electrodes are configured to deliver a reference signal of fluid flowing within the substantially cylindrical structure.

Clause 25: The medical probe according to any one of clauses 1-24, further comprising irrigation openings disposed proximate the distal end of the tubular shaft, the irrigation openings configured to deliver an irrigation fluid to the one or more electrodes.

Clause 26: The medical probe according to any one of clauses 1-25, wherein the plurality of spines comprise nitinol.

Clause 27: The medical probe according to any one of clauses 1-25, wherein the plurality of spines comprise metallic strands.

Clause 28: The medical probe according to any one of clauses 1-27, wherein the one or more strips of flexible circuit substrate comprises nitinol.

Clause 29: The medical probe according to any one of clauses 1-27, wherein the one or more strips of flexible circuit substrate comprises an inert biocompatible polymer.

Clause 30: The medical probe according to clause 29, the inert biocompatible polymer selected from the group consisting of polyethylbenzene, polydimethylsiloxane, polyglycolic acid, poly-L-lactic acid, polycaprolactive, polyhydroxybutyrate, polyhydroxyvalerate, polydioxanone, polyamides, polyimides, ethylene vinyl acetates, polyvinylidene fluoride, polycarbonate, polypropylene, polyethylene, polyurethane, polyethylene terephthalate, polyethylene naphthalate, polyanhydride, polycaprolactone, polydioxanone, polybutyrolactone, polyvalerolactone, poly(lactide-co-glycolide), polydimethylsiloxane, silicone, epoxy, fluoropolymer, polytetrafluoroethylene, or combinations thereof.

Clause 31: A method of constructing a medical probe, the method comprising: fabricating a flexible circuit substrate into one or more strips; positioning the one or more strips over a substantially cylindrical structure comprising a plurality of spines; and configuring the plurality of spines to extend radially outward from a tubular configuration along a longitudinal axis to define a substantially cylindrical structure.

Clause 32: The method according to clause 31, further comprising: cutting the one or more strips of flexible circuit substrate having a joined central point; and positioning the joined central point at a distal end of the substantially cylindrical structure.

Clause 33: The method according to any one of clauses 31 or 32, further comprising fastening the one or more strips of flexible circuit substrate to the substantially cylindrical structure.

Clause 34: The method according to clause 33, further comprising hinging the one or more strips of flexible circuit substrate to a distal ring at the distal end of the substantially cylindrical structure.

Clause 35: The method according to clause 34, further comprising sewing at least a portion of the one or more strips of flexible circuit substrate to the plurality of spines.

Clause 36: The method according to clause 33, further comprising attaching the one or more strips of flexible circuit substrate to one or more rivets located along the plurality of spines.

Clause 37: The method according to any one of clauses 31-33, further comprising fastening the one or more strips of flexible circuit substrate to an internal surface and an external surface of the substantially cylindrical structure.

Clause 38: The method according to any one of clauses 31-37, further comprising connecting one or more electrical traces from the flexible circuit substrate to wires running through a tubular shaft of the medical probe.

Clause 39: The method according to any one of clauses 31-38, further comprising printing one or more strips of flexible circuit substrate by physical vapor deposition.

Clause 40: The method according to any one of clauses 31-38, further comprising cutting one or more strips of flexible circuit substrate from a planar sheet comprising nitinol.

Clause 41: The method according to any one of clauses 31-40, further comprising positioning one or more electromagnetic location coils on the plurality of spines of the substantially cylindrical structure.

Clause 42: The method according to any one of clauses 31-41, further comprising forming cutouts along a length of a hollow tube to form the plurality of spines that, when compressing a distal end and a proximal end of the tube, the plurality of spines bend axially to form the substantially cylindrical structure.

Clause 43: The method according to clause 42, wherein the cutouts along the length of the hollow tube form the plurality of spines comprising a trifurcation point positioned between the proximal end and the distal end of the tube.

Clause 44: The method according to clause 43, wherein the cutouts along the length of the hollow tube further comprise a bifurcation point positioned on a spine branch extending from the trifurcation point, the bifurcation point positioned between the proximal end and the distal end of the tube.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A medical probe, comprising:
  a substantially cylindrical structure comprising:
    a proximal circular base;

a distal circular base substantially parallel to the proximal circular base;
    a plurality of spines extending along a longitudinal axis, joining the distal circular base and proximal circular base, each spine comprising:
      a trifurcation point positioned along at least a portion of the spine, and
      a spine branch extending from the trifurcation point and further comprising a bifurcation point; and
    one or more strips of flexible circuit substrate coupled to one or more of the plurality of spines.

2. The medical probe according to claim 1, each spine of the plurality of spines joined at a distal end of the substantially cylindrical structure.

3. The medical probe according to claim 1, the plurality of spines configured to move from a tubular configuration to an expanded cylindrical configuration.

4. The medical probe according to claim 1, the substantially cylindrical structure comprising a substantially planar distal portion circular base.

5. The medical probe according to claim 1, the substantially cylindrical structure comprising a middle portion between the distal circular base and the proximal circular base, the middle portion comprising a length ranging from about 10 mm to about 20 mm.

6. The medical probe according to claim 1, wherein the plurality of spines run linear along the longitudinal axis.

7. The medical probe according to claim 1, wherein the plurality of spines run sinusoidal along the longitudinal axis.

8. The medical probe according to claim 1, each spine converging into a distal ring at a distal end of the substantially cylindrical structure and a proximal ring at a proximal end of the substantially cylindrical structure.

9. The medical probe according to claim 1, the substantially cylindrical structure further comprising one or more electromagnetic location coils on one or more of the plurality of spines.

10. The medical probe according to claim 1, the one or more strips of flexible circuit substrate further comprising one or more conductive traces disposed on a surface of the flexible circuit substrate.

11. The medical probe according to claim 1, wherein the strips of flexible circuit substrate comprise one or more electrodes coupled to an external surface of the flexible circuit substrate.

12. The medical probe according to claim 11, the strips of flexible circuit substrate further comprising one or more reference electrodes coupled to an internal surface of the flexible circuit substrate such that the reference electrodes are co-located with respective electrodes on the external surface to define a stacked pair of electrodes.

13. The medical probe according to claim 11, wherein the one or more electrodes are configured to deliver a reference signal of fluid flowing within the substantially cylindrical structure.

14. A method of constructing a medical probe, the method comprising:
  fabricating a flexible circuit substrate into one or more strips;
  positioning the one or more strips over a substantially cylindrical structure comprising a proximal circular base, a distal circular base substantially parallel to the proximal circular base, and a plurality of spines, each spine comprising (i) a trifurcation point positioned along at least a portion of the spine and (ii) a spine branch extending from the trifurcation point and further comprising a bifurcation point;

coupling each strip of flexible circuit substrate to a respective spine of the plurality of spines; and configuring the plurality of spines to extend radially outward from a tubular configuration along a longitudinal axis to define the substantially cylindrical structure.

15. The method according to claim 14, further comprising:

cutting the one or more strips of flexible circuit substrate having a joined central point; and positioning the joined central point at a distal end of the substantially cylindrical structure.

16. The method according to claim 15, further comprising hinging the one or more strips of flexible circuit substrate to a distal ring at the distal end of the substantially cylindrical structure.

17. The method according to claim 14, further comprising printing one or more strips of flexible circuit substrate by physical vapor deposition.

18. The method according to claim 14, further comprising forming cutouts along a length of a hollow tube to form the plurality of spines that, when compressing a distal end and a proximal end of the hollow tube, the plurality of spines bend axially to form the substantially cylindrical structure.

19. The method according to claim 18, wherein the cutouts along the length of the hollow tube form the plurality of spines comprising the trifurcation point positioned between the proximal end and the distal end of the hollow tube.

* * * * *